US011452755B2

(12) United States Patent
Cheng et al.

(10) Patent No.: US 11,452,755 B2
(45) Date of Patent: *Sep. 27, 2022

(54) USE OF PHY906 AS TREATMENT FOR INFLAMMATORY BOWEL DISEASE AND/OR IRRITABLE BOWEL SYNDROME

(71) Applicant: YALE UNIVERSITY, New Haven, CT (US)

(72) Inventors: Yung-Chi Cheng, Woodbridge, CT (US); Shwu-Huey Liu, Madison, CT (US); Robert Tilton, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/083,864

(22) Filed: Oct. 29, 2020

(65) Prior Publication Data

US 2021/0106643 A1     Apr. 15, 2021

Related U.S. Application Data

(63) Continuation of application No. 16/051,008, filed on Jul. 31, 2018, now Pat. No. 10,849,951, which is a continuation of application No. 14/605,180, filed on Jan. 26, 2015, now Pat. No. 10,058,581.

(51) Int. Cl.
| | | |
|---|---|---|
| *A61K 36/00* | (2006.01) | |
| *A61K 36/725* | (2006.01) | |
| *A61K 36/484* | (2006.01) | |
| *A61K 36/539* | (2006.01) | |
| *A61K 36/65* | (2006.01) | |

(52) U.S. Cl.
CPC .......... *A61K 36/725* (2013.01); *A61K 36/484* (2013.01); *A61K 36/539* (2013.01); *A61K 36/65* (2013.01)

(58) Field of Classification Search
CPC ................... A61P 1/00; A61P 1/12; A61P 1/04
See application file for complete search history.

(56) References Cited

U.S. PATENT DOCUMENTS

| | | | |
|---|---|---|---|
| 4,618,495 A | 10/1986 | Okuda et al. | |
| 5,563,133 A | 10/1996 | Hipskind | |
| 5,665,393 A | 9/1997 | Chen et al. | |
| 6,048,847 A | 4/2000 | Ramadoss et al. | |
| RE37,262 E | 7/2001 | Yu et al. | |
| 6,492,425 B1 | 12/2002 | Callahan et al. | |
| 6,630,176 B2 | 10/2003 | Li et al. | |
| 7,025,993 B2 | 4/2006 | Cheng et al. | |
| 2003/0157126 A1 | 8/2003 | Li et al. | |
| 2005/0004155 A1 | 1/2005 | Boyd et al. | |
| 2005/0196473 A1 | 9/2005 | Cheng et al. | |
| 2006/0148786 A1* | 7/2006 | Lundeen | A61K 45/06 514/225.2 |
| 2006/0281818 A1 | 12/2006 | Ueno et al. | |

FOREIGN PATENT DOCUMENTS

| | | | |
|---|---|---|---|
| CN | 1430999 A | * | 7/2003 |
| EP | 1 811 303 A2 | | 7/2007 |
| JP | 62026229 A | * | 2/1987 |
| WO | 2008/101079 A1 | | 8/2006 |
| WO | 09/152228 A1 | | 12/2009 |

OTHER PUBLICATIONS

Loftus EV. Clinical epidemiology of inflammatory bowel disease: incidence, prevalence, and environmental influences. Gastroenterology, 2004;126:1504-1517.
Takasuna K, et al. Involvement of B-glucuronidase in intestinal microflora in the intestinal toxicity of the antitumor camptothecin derivative irinotecan hydroclonide (CPT-11) in rats. Cancer Res, 1996;56:3752-3757.
Araki E, et al. Relationship between development of diarrhea and the concentration of Sn-38, an active metabolite of CPT-II, in the intestine and blood plasma of athymic mice following intraperitoneal administration of CPT-II. Jpn J Cancer Res, 1993;84:697-702.
Collins JG. Prevalence of selected chronic conditions: United States, 1990-1992. Natl Center for Health Statistics. Vital Health Stat, 1997;10:194.
Aminosalicylates. Crohn's and Colitis Foundation of America (CCFA) Website, updates Feb. 2006. Available at http://www.ccfa.org/info/treatment/aminosalicylates.
Corticosteroids. Crohn's and Colitis Foundation of America (CCFA) Website, updates Feb. 2006. Available at http://www.ccfa.org/info/treatment/corticosteroids.
Immunomodulators. Crohn's and Colitis Foundation of America (CCFA) Website, updates Feb. 2006. Available at http://www.ccfa.org/info/treatment/immunomodulators.
Antibiotics. Crohn's and Colitis Foundation of America (CCFA) Website, updates Feb. 2006. Available at http://www.ccfa.org/info/treatment/antibiotics.
Biologies. Crohn's and Colitis Foundation of America (CCFA) Website, updates Feb. 2006. Available at http://www.ccfa.org/info/treatment/biologics.
Marita M, et al. Inhibition of beta-glucuronidase by natural glucuronides of Kampo medicines using glucoronide of SN-38 (7-ethyl-10-hydroxycamptothecin) as a substrale. Xenobiotica, 1993;23:5-10.
Farrell MP, Kummar S. Phase I/IIA randomized study of PHY906, a novel herbal agent, as a modulator of chemotherapy in patients with advanced colorectal cancer. CLin Colorectal Cancer, 2003;2:253-256.
Kosterlitz HW, Lee GM. Pharmacological analysis of intrinsic intestinal reflexes. Pharmacol Rev, 1964;16:301-309.

(Continued)

*Primary Examiner* — Qiuwen Mi
(74) *Attorney, Agent, or Firm* — Henry D. Coleman; R. Neil Sudol

(57) ABSTRACT

The present invention includes a method of using PHY906 for treating a bowel disorder including inflammatory bowel disease and irritable bowel syndrome. Particularly, the present invention provides a multiple symptoms treatment for the bowel disorder.

24 Claims, 3 Drawing Sheets

(56) References Cited

OTHER PUBLICATIONS

Gray AC, et al. Characterisation of opioid receptors involved in modulating circular and longitudinal muscle contraction in the rat ileum. Br. J. Pharmacol, 2005;144:687-694.

Atkinson W, et al. Food elimination based on IgG antibodies in irritable bowel syndrome: a randomized control trial. Gut, 2004;53:1459-1464.

Zar S, et al. Food-specific IgG4 antibody-guided exclusion diet improves symptoms and rectal compliance in irritable bowel syndrome. Scand J Gastroenterol, 2005;40:800-807.

Naliboff BD, et al. Evidence for two distince perceptual alterations in irritable bowel syndrome. Gut, 1997;41:505-512.

Caldarella MP, et al. Visceral sensitivity and symptoms in patients with constipation- or diarrhea-predominant irritable bowel syndrome (IBS): effect of a low-fat intraduodenal infusion. Amer J Gastroenterol, 2005;100:383-389.

Francis CY, Whorwell PJ. Bran and irritable bowel syndrome: time for reappraisal. Lancet, 1994;344:39-40.

Okano S, et al. Effects of tachykinin NK1 receptor receptor antagonists on the viscerosensory response caused colorectal distention in rabbits. J Pharmacol Exptl Ther, 2002;300:925-931.

Zar S, et al. Food-specific IgG4 and IgE titers to common food antigens in irritable bowel syndrome. Amer J Gastroenterol, 2005;100:1550-1557.

Quigley EM. Germs, gas and the gut: the evolving role of enteric flora in IBS. Amer J Gastroenterol, 2006;101:334-335.

Sharara AL, et al. A randomized double-blind placebo-controlled trial of rifaximin in patients with abdominal bloating and flatulence. Amer J Gastroenterol, 2006;101:326-333.

Niedzielin K, et al. A controlled, double-blind, randomized study on the efficacy of Lactobacillus plantarum LP299V in aptients with irritable bowel syndrome. Europ J Gastroenterol Hepatol, 2001;13:1143-1147.

Sonea IM, et al. Treatment with neurokinin-I receptor antagonist reduces severity of inflammatory bowel disease induced by Cryptospiridium parvum. Clin Diag Lab Immunol, 2002;9:333-340.

Sung JJ. Acupuncture for gastrointestinal disorders: myth or magic. Gut, 2002;51:617-619.

Schneider A, et al. Acupuncture treatment in irritable bowel syndrome. Gut, 2006;55:649-654.

Bensoussan A, et al. Treatment of irritable bowel syndrome with Chinese herbal medicine: a randomized controlled trial J Amer Med Assoc, 1998;280:1585-1589.

Strober W, et al. Reciprocal IFN-y and TGF-B responses regulate the occurrence of mucosal inflammation. Immunol Today, 1997;18:61-64.

Van Dullemen, et al. Treatment of Crohn's disease with anti-tumor necrosis factor chimeric monoclonal antibody. Gastroenterology, 1995;109:129-135.

Neurath MF, et al. Role of NF-κB in immune and inflammatory responses in the gut. Gut, 1998;43:856-860.

Scheinman RI, et al. Role of transcriptional activation of IkBa in mediation of immunosuppression by glucocorticoids. Science, 1995;270:283-286.

Hsu HY, Hsu CS. Commonly Used Formulas—with Illustrations. Oriental Healing Art Inst, Los Angeles, 1980.

Auphan N, et al. Immuno-suppression by glucocorticoids: inhibition of NF-κB activity through infuction of IkBa synthesis. Science, 1995;270:286-290.

Saltz LB, et al. Irinotecan plus fluorouracil and leucovorin for metastatic colorectal cancer. New Engl J Med, 2000;343:905-914.

Hecht JR. Gastrointestinal toxicity of irinotecan. Oncology, 1998;12:72-78.

Rothenberg ML, et al. A multicenter, phase II trial of weekly irinotecan (CPT-11) in patients with previously treated colorectal carcinoma. Cancer, 1999;85:786-795.

Rivory LP, et al. Conversion of irinotecan (CPT-11) to its active metabolite, 7-ethyl-10-hydroxycamptothecin (SN-38) by human liver carboxylesterase Biochem Pharacal, 1996;52:1103-1111.

Atsumi R, et al. Identification of the metabolites of irinotecan, a new derivative of camptothecin, in rat bile and its biliary excretion. Xenobiotica, 1991;21:1159-1169.

PCT International Search Report and Written Opinion from PCT/08/81283, dated Jan. 26, 2009.

Junsheng Xi, Clinical Research of Scutellaria Soup for the Treatment of Ulcerative Colitis, Thesis for Doctor Degree of Beijing University of Chinese Medicine, published on Nov. 30, 2006.

Taguchi et al., "Selective Postoperative Inhibition of Gastrointestinal Opioid Receptors", The New England Journal of Medicine, Sep. 27, 2001. 345:935-940.

Ouyang et al., "Therapeutic Roles of Acupuncture to Functional Gastrointestinal Disorders", Alimentary Pharmanology and Therapeutics, Oct. 15, 2004. 20(8):831-841.

European Search Report from European Patent Application No. 08842017.9, dated May 7, 2012.

Liu et al., "PHY906 in hepatocellular carcinoma", Proceedings of the American Association for Cancer Research Annual Meeting, vol. 48, Apr. 2007, p. 439.

Yen et al., "Phase I/II Study of PHY906/Capecitabine in Advanced Hepatocellular Carcinoma", Anticancer Research 29:4083-4092, 2009.

Alsamarai et al., "A Phase I study of PHY906 as a modulator of irinotecan (CPT-11) in patients with advanced solid tumors", J. of Clinical Oncology, May 2010, 20 (15)suppl. e 13571.

Farrell et al., "Phase I/II A Randomized Study of PHY 906, a Novel Herbal Agent, as a Modulator of Chemotherapy in Patients with Advanced Colorectal Cancer", Clinical Colorectal Cancer, Feb. 2003 2(4):253-256.

Kummar et al., "A Phase I Study of the Chinese Herbal Medicine PHY906 as a Modulator of Irinotecan-based Chemotherapy to Patients with Advanced Colorectal Cancer", Clinical Colorectal Cancer, Jun. 2011. 10(2):85-96.

Liu et al., "R&D and Clinical trial of PHY906 in the USA", Presented at GP-TCM Congress in Leiden, Netherlands, Apr. 16, 2012.

Lam et al., "The Four-Herb Chinese Medicine PHY906 Reduces Chemotherapy-Induced Gastrointestinal Toxicity", Sci Transl Med 2, 45ra69 (2010).

Sommadossi et al., "Modulation of 5-Fluororacil Catabolism in Isolated Rat Hepatocytes with Enhancement of 5-Fluororacil Glucuronide Formation", Cancer Res 1985;45:116-121, (1985).

Saif et al., "Phase 1 study of the botanical formulation PHY906 with capecitabine in advanced pancreatic and other gastrointestinal malignancies", Phytomedicine (2010).

Liu et al., "Developing PHY906 as a broad-spectrum modulator of chemotherapeutic agents in cancer therapy", Proc Amer Assoc Cancer Res, vol. 45, 2004.

Liu et al., "Old formula, new Rx: The journey of PHY906 as cancer adjuvant therapy", Journal of Ethnopharmacology 146(2012):614-623.

Liu et al., "Botanical activity relationship in traditional Chinese medicine:Studies of PHY906 as an adjuvant therapy with cancer chemotherapeutic agents",93rd Annual Meeting of the American Association for Cancer Research, Apr. 6-10, 2002, San Francisco, CA.

Tilton et al., "A comprehensive platform quality control of botanical drugs (PhytomicsQC): a case study of Huangqin Tang (HQT) and PHY906", Chinese Medicine 2010, 5:30.

Hande et al., "Metabolism and Excretion of Etoposide in Isolated, Perfused Rai Liver Models", Cancer Research 1988:48:5692-5695.

Rockwell et al., Poster from the meeting of the Radiation Research Society in Maui Sep. 25-29, 2010.

Huang et al., The Pharmacology of Chinese Herbs, 1999.

* cited by examiner

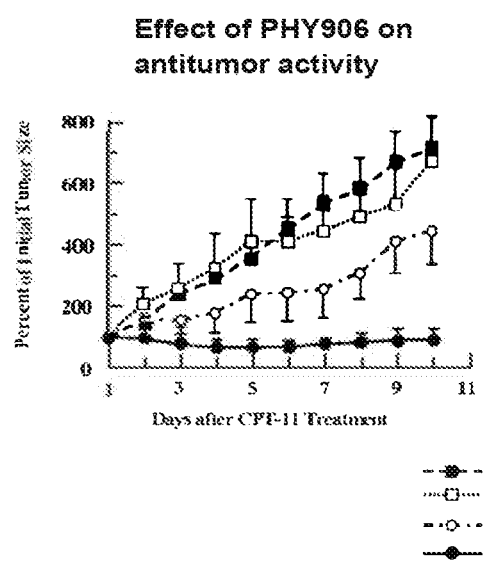
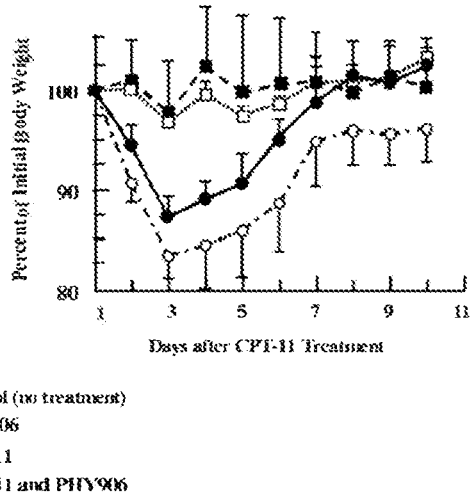
Figure 1A
Effect of PHY906 on antitumor activity
Figure 1B
Effect of PHY906 on toxicity Effect of PHY906 on Mortality

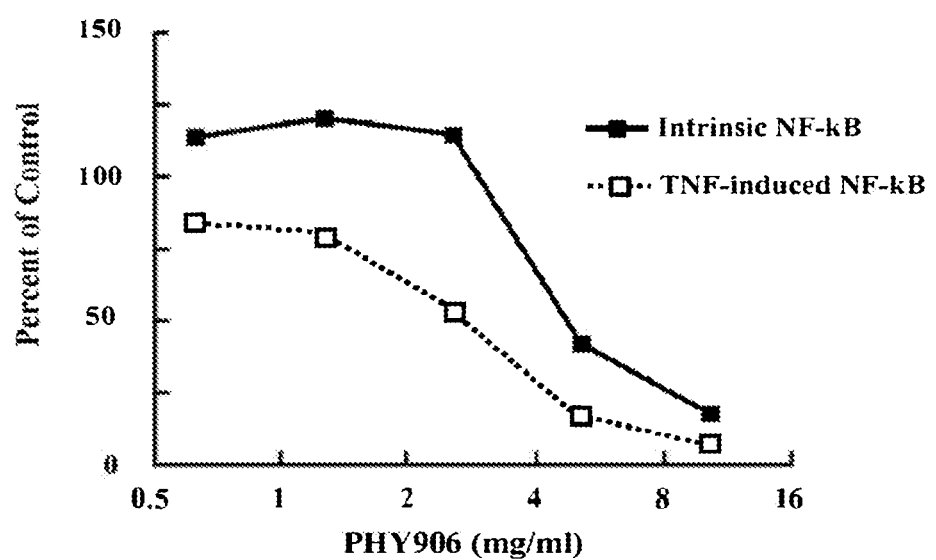

USE OF PHY906 AS TREATMENT FOR INFLAMMATORY BOWEL DISEASE AND/OR IRRITABLE BOWEL SYNDROME

RELATED PATENT AND APPLICATIONS

This application is a continuation of U.S. application Ser. No. 16/051,008, filed on Jul. 31, 2018, which is a continuation of U.S. patent application Ser. No. 14/605,180 filed Jan. 26, 2015, which issued on Aug. 28, 2018 as U.S. Pat. No. 10,058,581, which is a continuation of U.S. patent application Ser. No. 12/739,591 filed Jan. 10, 2011, which is a 371 of PCT/US2008/081283, filed Oct. 27, 2008 which claims benefit to U.S. Provisional Patent Application No. 60/982,608, filed on Oct. 25, 2007 and entitled "Use of PHY906 as Treatment for Inflammatory Bowel Disease and/or Irritable Bowel Syndrome", which applications are herein incorporated by reference in their entirety.

This application is related to U.S. patent application Ser. No. 09/522,055, entitled "Herbal Composition PHY-906 and Its Use in Chemotherapy", which was filed on Mar. 9, 2000 and abandoned; International Application PCT/US01/07353, entitled "Herbal Composition PHY906 and Its Use in Chemotherapy", which was filed Mar. 8, 2001 and published as WO 2001/66123; U.S. Provisional Patent Application No. 60/625,943 filed on Nov. 9, 2004 and entitled "Herbal Composition PHY-906 and Its Use in Chemotherapy"; U.S. patent application Ser. No. 11/100,433, entitled "Herbal Composition PHY906 and Its Use in Chemotherapy", which was filed on Apr. 7, 2005 and published as U.S. 2005/0196473A1; International Application PCT/US05/40605, filed on Nov. 9, 2005 and published as WO 2006/53049; and U.S. Pat. No. 7,025,993, entitled "Herbal Composition PHY906 and Its Use in Chemotherapy", which was issued on Apr. 11, 2006; all of which are herein incorporated by reference in their entirety.

FIELD OF THE INVENTION

The present invention relates to the use of PHY906 for treating a bowel disorder, such as, for example, inflammatory bowel disease (IBD) and irritable bowel syndrome (IBS).

BACKGROUND OF THE INVENTION

1. Inflammatory Bowel Disease

Inflammatory bowel disease (IBD) encompasses a group of conditions that exhibit inflammation of the large and, in some cases, small intestine. The two main forms of IBD are Crohn's disease and ulcerative colitis (UC). Other much less common manifestations of IBD are collagenous colitis, lymphocytic colitis, ischaemic colitis, diversion colitis, Behcet's syndrome, infective colitis, and indeterminate colitis. Diagnosis is generally by colonoscopy with biopsy of pathological lesions.

In the US, in 2001, the prevalence of Crohn's disease and UC was 162 and 246 cases per 100,000, respectively[1]. Although the mortality rate from IBD is low, hospitalizations for 2002 totaled 169,000 (62% for Crohn's disease) and ambulatory care visits approximated 5.9 million per year in 1999-2000[2,3]. In the early 1990s, over 160,000 people in the US with IBD were considered disabled[4].

The majority of Crohn's cases start in the terminal ileum, but it can affect any part of the gastrointestinal tract. In contrast, UC is restricted to the colon. From a microscopic point of view, whereas Crohn's disease affects the entire bowel wall, UC is restricted to the epithelial lining of the gut. Both UC and Crohn's show extra-intestinal manifestations, e.g. liver problems, arthritis, eye problems, skin manifestations, they are present in different proportions in each disease.

Most medical treatment for IBD is aimed at controlling the ongoing inflammation and is directed to achieving and maintaining remission. Since the symptoms, course of disease, and prognosis vary from patient to patient, no standard treatment exists for IBD. An accurate diagnosis, usually achieved through the use of endoscopic, radiological, and pathologic examinations, is imperative for designing a proper course of treatment. Currently, for IBD, the five main classes of medications used are: aminosalicylates, corticosteroids, immunomodulators, antibiotics, and biologies[5].

Aminosalicylates:

Aminosalicylates are effective in treating mild to moderate cases of IBD as well as preventing relapses and maintaining remission. They are usually administered orally or rectally. Sulfasalazine (Azulfidine®), the first aminosalicylate to be widely used for IBD, is effective in achieving and maintaining remission in people with mild-to-moderate disease. It delivers 5-aminosalicylic acid (5-ASA) to the intestine but comes with disagreeable side effects in some patients, such as headache, nausea, loss of appetite, vomiting, rash, fever, and decreased white blood cell count. Sulfasalazine can decrease sperm production and function in men while they are taking the medication. It has been associated with pancreatitis in rare cases. The headaches, nausea, and rash are thought to be due to the release of the sulfapyridine moiety that is necessary for delivery of the 5-ASA to the intestine.

Other derivates of 5-ASA have also been synthesized. Those derivatives include mesalamine (Asacol®, Pentasa®), olsalazine (Dipentum®), and balsalazide (Colazal™). Local mesalamine preparations bypass the stomach to avoid early digestion, and then release close to the inflamed section of the bowel. Oral, delayed-release preparations such as Pentasa® and Asacol® can release 5-ASA directly to the small intestine and colon, or to the ileum and/or colon, respectively. Rowasa®, an enema formulation of mesalamine, allows the drug to be applied directly to the left colon. Rowasa® is effective in 80% of patients with mild-to-moderate colitis that affects only the left side of the colon. Mesalamine suppositories (Canasa®) that deliver the drug directly from the rectum up to the sigmoid colon are effective in a high proportion of patients with UC limited to the rectum and the lower end of the colon. Dipentum®, an oral, delayed-release preparation of olsalazine, delivers 5-ASA directly to the colon only.

Corticosteroids:

As fast-acting anti-inflammatory and immunosuppressive agents, corticosteroids have been used for treating acute flare-ups of IBD for over 50 years. Since that time, these powerful agents have been the mainstay of treatment for disease. Most patients notice an improvement in symptoms within days of starting corticosteroids[6]. This group of medications is available in oral, rectal, and intravenous (IV) forms. Corticosteroids are not effective in preventing flare-ups and therefore are rarely used for maintenance therapy in IBD. Since long-term use results in side effects, these agents are recommended only for short-term use in order to achieve remission, but they are not used frequently in the latter case. For people with moderate to severe active disease, oral corticosteroids include prednisone (Deltasone®), methylprednisolone (Medrol®), and hydrocortisone. Aminosalicylates are often taken together with corticosteroids.

Budesonide (Entocort®), an oral corticosteroid, is used to treat mild-to-moderate Crohn's disease involving the end of the small intestine and/or the first part of the large intestine. This nonsystemic steroid targets the intestine rather than the whole body. Corticosteroids may also be given rectally as enemas (hydrocortisone, methylprednisone, Cortenema®), foams (hydrocortisone acetate, ProctoFoam-HC®), and suppositories. Such preparations are used for mild-to-moderate ulcerative colitis that is limited to the rectum or lower part of the colon. When used in combination with other therapies, these agents are also effective against more widespread disease that starts at the rectum. Methylprednisone and hydrocortisone are often given by IV infusion to patients with severe and extensive disease. Acute IBD does not respond to corticosteroid therapy in 20-30% of cases and in 30-40% of cases with moderate to severe disease, corticosteroids cannot be abruptly discontinued without occurrence of a disease flare-up.

Immunomodulators:

Since IBD appears to be caused by an overactive immune system, immunomodulators play an important role in the treatment of this disease[7]. These drugs are used for those who have one of the following characteristics: (a) side effects with corticosteroid treatment, (b) steroid-dependent disease, (c) do not respond to aminosalicylates, antibiotics, or corticosteroids, (d) perineal disease that does not respond to antibiotics, and (e) need to maintain remission. These drugs may be combined with a corticosteroid to speed up response during active flares of disease.

Azathioprine (Imuran®, Azasan®) and 6-mercaptopurine (6-MP, Purinethol®) are oral immunomodulators that are used to maintain remission in Crohn's disease and UC. Since these agents have a slow onset of action, they are usually given along with another faster-acting drugs, e.g. corticosteroids. Other immunomodulators used for IBD are cyclosporine A (Sandimmune®, Neoral®) and tacrolimus (Prograf®). Of these agents, cyclosporine A has the fastest onset of action. When given IV at high doses, cyclosporine A is useful against active Crohn's disease. This drug is effective against severe UC as is tacrolimus. The latter agent can be used against Crohn's when corticosteroids are not effective or when fistulas develop. Tacrolimus may be applied topically to treat Crohn's disease of the mouth or perineal area. An option for people with Crohn's disease who do not respond to other treatments and cannot tolerate other immunosuppressants is IV-administered Methotrexate (MTX, Rheumatrex®, Mexate®)).

Antibiotics:

Although no specific infectious agent has been identified as the cause of IBD, antibiotics are frequently used as a primary treatment[8]. Antibiotics are effective as long-term therapy in Crohn's disease patients who have fistulas (between loops of intestine or between intestine and adjacent organs, e.g. skin) or recurrent abscesses near the anus. Patients whose active disease is successfully treated with antibiotics may be kept on these as maintenance therapy. Generally, antibiotics are not considered useful for those with UC; the exception is toxic megacolon.

The most frequently prescribed broad-spectrum antibiotics for IBD are metronidazole (Flagyl®) and ciprofloxacin (Cipro®). Metronidazole is a primary therapy for active Crohn's and has been shown to reduce the recurrence of Crohn's for the first three months after ileum resection surgery. This drug is effective in managing perineal Crohn's in over 50% of cases. Ciprofloxacin, much safer than metronidazole, is commonly used to treat active Crohn's disease. Both oral and IV metronidazole and ciprofloxacin are used for IBD treatment.

Biologics:

Possible targets by which biologics may interfere with the body's inflammatory response in IBD include tumor necrosis factor-alpha (TNF-u), interleukins, adhesion molecules, colony-stimulating factors, and others[9]. Since their mechanism is targeted, biologic therapies offer a distinct advantage in IBD treatment. Unlike corticosteroids, which tend to suppress the entire immune system and thereby produce major side effects, biologic agents act selectively. Biologics are targeted to particular enzymes and proteins that have already been proven defective, deficient, or excessive in people with IBD or in animal models of colitis.

Anti-TNF agents have been used in both Crohn's disease and UC. The chimeric monoclonal antibody Infliximab (Remicade®) is approved for Crohn's disease and fistulizing Crohn's disease, as well as for UC. Given as an IV drip, it is used for people with moderately-to-severely active disease who have not responded well to other therapies. Adalimumab (Humira®), a fully human monoclonal antibody given by injection, is used for people with moderately to severely active Crohn's disease who have not responded well to other therapies and who have lost response or are unable to tolerate infliximab. Certolizumab pegol (currently known as Cimzialm), is currently being investigated for use in Crohn's disease.

Adhesion molecule inhibitors are being evaluated as IBD therapies. These drugs work by binding to particular cells in the bloodstream that are key players in inflammation. Natalizumab (Tysabri®), already approved for multiple sclerosis, is an adhesion molecule inhibitor currently under investigation for the treatment of Crohn's disease.

Visilizumab (Nuvion®), a humanized monoclonal antibody directed against CD3 receptors on activated T cells, and alicaforsen, a drug that inhibits ICAM-1 (plays a key role in intestinal inflammation) are currently being investigated as possible treatments for UC. Other potential IBD agents include thalidomide, the interleukins IL-6, IL-10, IL-11, and IL-12, interferon gamma, and granulocyte-macrophage colony-stimulating factor (GM-CSF).

Surgery:

In spite of the above medication options for IBD, 66-75% of Crohn's patients and 25-40% of those with UC will eventually undergo surgery[10,11] Surgery for Crohn's disease depends upon the location of the disease. If it is in the small intestine, areas of diseased bowel may alternate with areas of normal bowel, The areas of active disease may narrow, forming strictures, which can block the passage of digested food. If the lesions are separated, strictureplasty is often used. Here, the structured areas are widened and the small intestine is spared. Resection and anastimosis may be needed if the stricture is long or if there are multiple strictures close to each other. Although resection may offer years of relief, disease can recur at or near the site of the anastimosis.

In patients with severe Crohn's in the colon, colectomy may be done. If the rectum is unaffected the end of the ileum may be rejoined to the rectum; thus, stool may be passed normally, If both the colon. and rectum are involved, proctocolectomy with subsequent ileostomy may be performed. Fistulas and/or abscesses eventually develop in about 25% of patients with Crohn's disease. If fistulas are unresponsive to medication, they are removed by resection of the affected bowel followed by anastimosis. Abscesses must be drained; in some cases, this requires resection. For years, the standard surgery for UC, has been proctocolectomy with ileostomy. Now the most common procedure is restorative proctocolectomy; this allows the patient to continue to pass stool through the anus. Unlike Crohn's disease, which can recur after surgery, UC is "cured" once the colon is removed.

2. Irritable Bowel Syndrome

Irritable bowel syndrome (IBS, spastic colon) is a functional bowel disorder characterized by abdominal pain and changes in bowel habits. Unlike IBD. IBS is not associated with abnormalities seen on clinical testing. The most frequent symptoms of IBS are the lower abdominal pain and bloating associated with alteration of bowel habits, and abdominal discomfort relieved by defecation. IBS is may be classified as diarrhea-predominant (IBS-D), constipation-predominant (IBS-C), or with alternating stool pattern (IBS-A). Sometimes, IBS may have an acute onset and develop after an infectious illness characterized by two or more of the following symptoms: fever, vomiting, acute diarrhea, and positive stool culture; this form, which has been termed post-infective IBS (IBS-PI), consists mostly of IBS-D.

Approximately 20 percent of people in the US have symptoms of IBS and these symptoms occur before the age of 35 in about 50 percent of cases 0). About one-third of all patients suffer from IBS-D. Although mortality from IBS is very low, hospitalizations in 2002 totaled 190,000, ambulatory care visits totaled 1.3 million per year in 1999-2000, and 46,000 patients with IBS were deemed disabled in 1990-1992[2-4]. In 1985, 2.2 million prescriptions per year were written for IBS[13]. IBS in general and IBS-D in particular have a significant negative impact on the quality of life (QOL) for the many people who suffer from this condition; it causes lost days from work and interferes significantly with home-based, social, and leisure activities.

IBS treatment involves reassuring patients that their disease is not life-threatening, giving dietary advice, and prescribing medication Immune response to some foods may play a role in the reduction or elimination of IBS symptoms in some cases$_{(14, 15)}$ IBS patients are sensitive to fats, insoluble fibers, caffeine, carbonation, alcohol, fructose, foods with elevated levels of IgG4 antibodies, and foods that may increase colonic contractions[15-20].

For IBS-C patients, medications include stool softeners and laxatives. For IBS-D sufferers, medications consist of antidiarrheals, e.g. opiods or opiod analogs (loperamide, ImodiumCGt; diphenoxylate; diphenoxylate plus atropine, Lomotil®). Severe cases may be treated with codeine or propoxyphene (Darvon®) and refractory cases may be treated with paregoric or even morphine. Low doses of tricyclic and selective serotonin reuptake inhibitory antidepressants are widely prescribed for the relief of pain and diarrhea, respectively. Alosetron (Lotronex®), a selective 5-HT3 antagonist is available for women in the US who have IBS-D only. Cilansctron (Calmactin®), another selective 5-HT3 antagonist, is currently in clinical trials in Europe for the treatment of IBS-D in both men and women. In 2005, the sponsor of cilansetron withdrew its application for approval from the US FDA on the basis of a "non-approvable" letter (additional clinical trials were requested). Tegaserod (Zelnorm®), a selective 5-HT4 antagonist for IBS-C, is the only agent approved to treat constipation, abdominal pain, and bloating in women in the US; it is not approved in the EU, however. The potential role of bacterial overgrowth in some patients with IBS is suggested by recent studies suggesting that rifaximin is an effective treatment for abdominal bloating and flatulence (21, 22).

Alternative treatments for IBS include probiotics (potentially beneficial strains of bacteria and yeast found in the human gut, e.g. *Lactobacillus planarinm* LP299V and *Bifidobacterium ifantis* (23, 24). Clinical studies with probiotics are currently being conducted in the US[25, 29].

3. Traditional Chinese Medicine for Treating Bowel Disorders

Mixtures of botanical extracts have been widely used throughout the world for the management of disease and are gaining increased acceptance in Western countries (35-38) The use of herbal Traditional Chinese Medicine (TCM) is based on many chemical components in an herbal preparation that interact and act simultaneously through multiple molecular targets and cellular mechanisms. These multiple components serve various functions; some may be responsible for efficacy while others may decrease toxicity or increase bioavailability. Chinese herbal formulations are perhaps the best-known botanical medicines to have been derived from empirical observations in humans over the millennia. The claimed indication of a given Chinese medicinal preparation is multiple rather than single. This is not surprising, many phytochemical ingredients in a formulation can exert actions at multiple targets and biological pathways.

Aspects of Traditional Chinese Medicine (TCM), including acupuncture and herbal medicines, have also been examined as possible IBS treatments. The benefits of acupuncture for the treatment of IBS have not been proven conclusively[30]. Many studies were not of adequate size and/or were uncontrolled or poorly controlled. In a well-controlled study of 43 IBS patients where the efficacy of acupuncture following the rules of TCM was compared with that of sham (placebo) acupuncture, an insignificant difference was seen between the two groups[31]. Two clinical studies on the effects of acupuncture on IBS have recently been completed in the US, but the results have not yet been published[32].

Several clinical studies in China have suggested the potential of TCM herbal formulations in the treatment of IBS, but these have lacked adequate trial design, poor randomization techniques, and/or lack of blinding[33]. In a randomized, placebo-controlled trial where 116 patients were treated with placebo, with a "standard" formulation of 20 herbs, or with "individualized" herbal formulations, patients treated with the herbal formulations had more symptom improvement than placebo controls[33]. In contrast, in a randomized double-blinded placebo-controlled trial involving 119 patients with IBS-D treated with either placebo or an eleven-herb TCM formulation, no significant difference was seen between the two arms in terms of global symptom improvement[34].

In summary, IBD and IBS are common chronic illnesses with multiple symptoms that can be very serious and debilitating. Numerous treatments for IBD and IBS have been developed, but most of these treatments do not have desirable efficacy or are single-symptom remedies.

SUMMARY OF TIE INVENTION

In one embodiment, the present invention provides a method of treating a bowel disorder comprising administering to a patient in need thereof a therapeutically effective amount of a composition comprising an herbal preparation having *Scutellaria, Glycyrrhiza, Ziziphus* and *Paeonia*.

In another embodiment, the present invention provides a method of inhibiting a 6-opioid receptor or a tachykinin NK-1 receptor by contacting the 6-opioid and tachykinin NK-1 receptors with a composition comprising an herbal preparation having Scutellaria, *Glycyrrhiza, Ziziphus* and *Paeonia*.

In another embodiment, the present invention provides a method of inhibiting a nuclear factor-kappa B (NF-KB) by contacting the NF-KB with a composition comprising an herbal preparation having *Scutellaria, Glycyrrhiza, Ziziphus* and *Paeonia*.

BRIEF DESCRIPTION OF THE DRAWINGS

FIG. 1A is a graph showing the change of initial tumor size after various days of CPT-11 treatment and thereby demonstrating the antitumor efficacy of the combination of PHY906 and CPT-11. Methods: A single bolus dose (360 mg/kg) of CPT-11 was administered to BDF-1 mice bearing murine Colon 38 tumors on day 0, 30 min after PHY906 (500 mg/kg). PHY906 administration was continued bid for 4 days. Treatment groups consisted of 5 mice each. FIG. 1A shows antitumor effects. Vertical lines indicate + (up) or − (down) one standard derivation (SD).

FIG. 1B is a graph showing the change of body weight after various days of CPT-II treatment and thereby demonstrating the reduction of CPT-11 toxicity by PHY906. Methods: A single bolus dose (360 mg/kg) of CPT-11 was administered to BDF-1 mice bearing murine Colon 38 tumors on day 0, 30 min after PHY906 (500 mg/kg). PHY906 administration was continued bid for 4 days. Treatment groups consisted of 5 mice each. FIG. 1B shows body weights. Vertical lines indicate + (up) or − (down) one standard derivation (SD).

FIG. 3 is a graph demonstrating the inhibitory effect of PHY906 against both intrinsic and TNF-induced NF-kB.

DETAILED DESCRIPTION OF THE INVENTION

Figure 2:
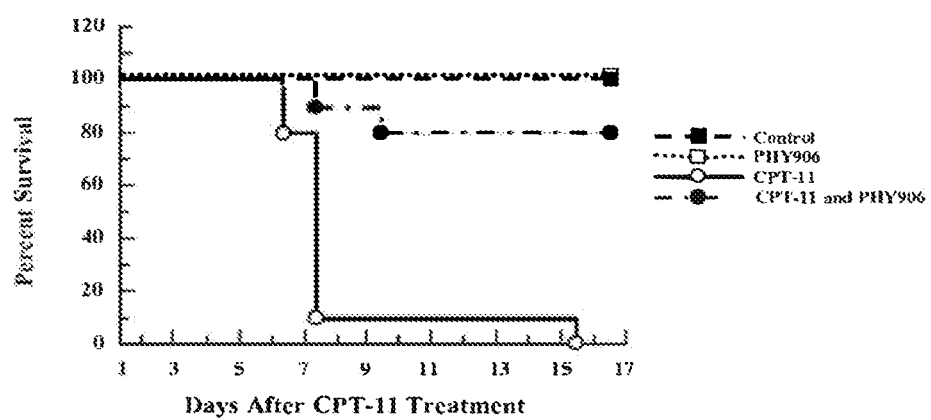
FIG. 2 is a Kaplan-Meyer survival curve demonstrating the reduction of toxicity CPT-11 toxicity by PHY906. Methods: A single bolus dose (360 mg/kg) of CPT-11 was administered to BDF-1 mice bearing murine Colon 38 tumors on day 0, 30 min after PHY906 (500 mg/kg). PHY906 administration was continued bid for 4 days. Treatment groups consisted of 5 mice each.

During a literature search of Chinese medicinal formulations that have been used to treat symptoms similar to those that are associated with modern cancer chemotherapy, PHY906 was selected from among the several formulations found. PHY906, a decoction of a mixture of four herbs, was established more than 1500 years ago for the treatment of diarrhea, abdominal spasms, fever, headache, vomiting, nausea, extreme thirst, and subcardial distention[39].

PHY906 includes at least four herbs commonly known as Scute, Licorice, Peony Alba and Ziziphi Fruit (Table 3). Thus, one plant species is chosen from each one of the four plant groups provided in Table 3 in order to produce the desired herbal compositions of the present invention. While particular combinations of the listed plant species are provided as examples of preferred PHY906 formulations, the compositions and methods of this invention encompass any combination of four plant species wherein a plant species is selected from each one of the four groups in Table 3. This invention encompasses any such combination of such herbs which have at least one of the biological activities or desired effects ascribed to PHY906 as described herein.

TABLE 1

Examples of Particular Species of Four Genera which can be Used to make PHY906.
Common English Name of TCM Herbal Group

| Scutellaria | Licorice | Peony Alba | Ziziphi Fruit |
| --- | --- | --- | --- |
| Anemone rivularis Buch.-Ham. ex DC. | Abrus mollis Hance | Paeonia delavayi Franch. var. lutea (Delavay ex Mill. Franch.) Finet et Gagnep. | Ziziphus jujuba Mill. |
| Thalictrum omelense W. T. Wang et S. H. Wang | Glycyrrhiza aspera Pall. | Paeonia lactiflora Pall. | Ziziphus jujuba Mill. var. inermis |
| Mahonia bealei (Fort.) Carr. | Glycyrrhiza eurycarpa P. C. Li | Paeonia mairei Levi. | |
| Nandina domestica Thunb. | Glycyrrhiza glabra L. | Paeonia obovata Maxim. var. willmottiae (Stapi) Stern | |
| Scutellaria amoena C. H. Wright | Glycyrrhiza inflata Bat. | Daphne papyracea Wall. ex Steud. | |
| Scutellaria amoena C. H. Wright var. cinerea Hand.-Mazz. Onuma | Glycyrrhiza squamulosa Franch. | Cynanchum otophyllum Schneid. | |
| Scutellaria baicalensis Georgi | Glycyrrhiza uralensis Fisch. | Codonopsis lanceolara Sieb. et Zucc. Trautv. | |
| Scutellaria baicalensis Georgi var. albiflora K. Scutellaria hypericifolia Levl Scutellaria likiangensia Diels Scutellaria obtusifolia Hemsl. var. trinervata (Vant.) C. Y. Wu et H. W. Li | Phlomis betonicoides Diels | | |

TABLE 1-continued

Examples of Particular Species of Four Genera which can be Used to make PHY906.
Common English Name of TCM Herbal Group

| Scutellaria | Licorice | Peony Alba | Ziziphi Fruit |
|---|---|---|---|
| *Scutellaria regeliana* Nakai | | | |
| *Scutellaria regeliana* Nakai var. *ikonnikovii* (Juz.) C. Y. Wu et H. W. Li | | | |
| *Scutellaria ehderiana* Diels | | | |
| *Scutellaria* Licorice Peony Alba Ziziphi Fruit *Scutellaria tenax* W. W. Smith var. *patentipilosa* (Hand.-Marz.) C. Y. Wu | | | |
| *Scutellaria viscidula* Bunge | | | |

In one embodiment, PHY906 includes *Scutellaria baicalensis* Georgi (scute baical skullcap root), *Paeonia lactiflora* Pall. (white peony root). *Glycyrrhiza uralensis* Fisch. (licorice root), and *Ziziphus jujube* Mill. (date fruit); which are mixed in a ratio of 1.5:1:1:1 by weight, respectively. Each of the four herbs of PHY906 is reported to possess a distinct pharmacological profile; these include anticancer and antiviral activity, hematological and immunological stimulation, analgesic activity, liver protection, and appetite improvement[40]. An alternative formulation of PHY906 has the herbs Scutellaria, *Glycyrrhiza, Ziziphus*, and *Paeonia* in the following relative proportions: 4/14:3/14:4/14:3/14, respectively.

While specific ratios of the herbs of PHY906 are provided as examples, the compositions and methods of this invention encompass any ratios of the four herbal components which have the desired biological activity as described herein.

In one embodiment, PHY906 can be produced by a process as described hereinbelow. First, the proper ratios of the ingredients of the herbal raw materials are placed in a jacketed reactor and extracted with water at an elevated constant temperature with mixing. The ratios are set forth in the Manufacturing Instruction reproduced from Master Formula Record. The solid materials are then separated from the liquid with a 120-mesh screen. The filtrate is collected and then concentrated by evaporating the water under reduced pressure. The concentrated liquor is spray dried at an elevated temperature to yield dry powder which is then processed to yield granulated powder. This bulk substance is then formulated into the desired dosage form.

Process controls are utilized to ensure the uniformity and integrity of the product. Such process controls include, but are not limited to, checking the volume of the process liquor, HPLC determinations to establish Chemical Fingerprintings to verify identity of the raw materials, and inspections and tests of intermediate and final products. Accepted Quality Level (AQL) Limits are established for each conducted analysis and for each step of the manufacturing and control of production. All of the components used in the production process are assigned a specific lot number in the Production Instruction Record. Quality control records are reviewed before a batch is released. Purified marker substances are used for identification and quality control of the raw materials as well as the herbal substances. Table 2 lists the marker substances of each raw material used in the preparation of PHY906 herbal substance.

TABLE 2

Marker Substances for Herbal Ingredients of PHY906

| Herb | Origin of Herb Producing Place | Marker Substance |
|---|---|---|
| *Scutellaria baicalensis* Georgi. | Shang Xi Province, China | Baicalin |
| *Glycyrrhiza uralensis* Fisch. | Inner Mongolia, China | Glycyrrhizin |
| *Ziziphus jujuba* Mill. | Hebei/Shangtong Province, China | Chelidonic Acid |
| *Paeonia lactiflora* Pall. | An Hwei Province, China | Paeoniflorin |

The compositions of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, the type of concurrent treatment, if any, the frequency of treatment, and the nature of the effect desired.

The pharmaceutical formulation for systemic administration according to the invention may be formulated for enteral, parenteral, or topical administration. Indeed, all three types of formulations may be used simultaneously to achieve systemic administration of the active ingredient. While individual needs vary, determination of optimal ranges of effective amounts of each component is within the skill of the art.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action.

PHY906 can be used in the form of a medicinal preparation, for example, in solid, semi-solid or liquid form which contains PHY906, as an active ingredient, in admixture with an organic or inorganic carrier or excipient suitable for external, enteral, or parenteral applications. The active ingredient may be compounded, for example, with the usual non-toxic pharmaceutically acceptable carriers for tablets, pellets, capsules, suppositories, solutions, emulsions, suspensions, and any other form suitable for use.

Formulations of the present invention encompass those which include talc, water, glucose, lactose, gum acacia, gelatin, mannitol, starch paste, magnesium trisilicate, corn starch, keratin, colloidal silica, potato starch, urea, and other carriers suitable for use in manufacturing preparations, in solid, semisolid or liquid form and in addition auxiliary, stabilizing, thickening and coloring agents, and perfumes may be used.

For preparing solid compositions such as tablets or capsules, PHY906 is mixed with a pharmaceutical carrier (e.g., conventional tableting ingredients such as corn starch, lactose, sucrose, sorbitol, talc, stearic acid, magnesium stearate, dicalcium phosphate or gums) and other pharmaceutical diluents (e.g., water) to form a solid preformulation composition containing a substantially homogeneous mixture of PHY906, or a non-toxic pharmaceutically acceptable salt thereof. When referring to the preformulation compositions as substantially homogenous, it is meant that the active ingredients are dispersed evenly throughout the composition so that the composition may be readily subdivided into equally effective unit dosage forms such as tablets, pills and capsules.

This solid preformulation composition is then subdivided into unit dosage forms of the type described above containing an effective amount of the composition of the present invention, preferably in capsules.

The tablets or pills containing PHY906 can be coated or otherwise compounded to provide a dosage form affording the advantage of prolonged action. For example, the tablet or pill can comprise an inner dosage an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings such materials including a number of polymeric acids and mixtures of polymeric acids with such materials as shellac, cetyl alcohol, and cellulose acetate.

The liquid forms, in which PHY906 may be incorporated for administration orally or by injection, include aqueous solution, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

For buccal administration, the compositions of the present invention may take the form of tablets or lozenges formulated in conventional manners.

PHY906 may also be formulated for parenteral administration by injection, which includes using conventional catheterization techniques or infusion. Formulations for injection may be presented in unit dosage form, e.g., in ampules, or in multi-dose containers, with an added preservative. The compositions may take such forms as suspensions, solutions or emulsions in oily or aqueous vehicles, and may contain formulating agents such as suspending, stabilizing, and/or dispersing agents. Alternatively, the active ingredients may be in powder form for reconstitution with a suitable vehicle, e.g., sterile pyrogen-free water, before use.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

Liposomes can also be used to encapsulate the agent for delivery into the cell.

In practicing the methods of this invention, PHY906 may be used alone or in combination, or in combination with other therapeutic or diagnostic agents. In certain preferred embodiments, the compounds of this invention may be coadministered along with other compounds typically prescribed for cancer chemotherapy according to generally accepted medical practice. The compounds of this invention can be utilized in vivo, ordinarily in mammals, such as humans, sheep, horses, cattle, pigs, dogs, cats, rats and mice, or in vitro.

Actual methods for preparing administrable compositions and adjustments necessary for administration to subjects will be known or apparent to those skilled in the art and are described in more detail in, for example, Remington's Pharmaceutical Science, 17th Ed., Mack Publishing Company, Easton, Pa. (1985), which is incorporated herein by reference.

PHY906 has proven to be efficacious in enhancing the therapeutic indices of a variety of anticancer agents including CPT-11 (irinotecan, Camptosar®). CPT-11 is a water-soluble derivative of camptothecin (an antitumor alkaloid isolated from *Camptobea acumiauta*) that exhibits a wide spectrum of antitumor activity because of its inhibition of DNA topoisomerase I[41] CPT-11 is a component of some of the most widely used chemotherapy treatment regimens (e.g. the "Saltz" regimen [CPT-11 plus 5-fluorouracil/leucovorin], IFL, FOLFIRI, AIO) for colorectal cancer[43-42]. Diarrhea has long been recognized as one of the most common limiting side effects associated with CPT-11 use, regardless of the schedule of administration[44-46]. It causes two types of diarrhea: (a) early acute diarrhea that occurs soon after CPT-11 administration and (b) late-onset diarrhea that occurs usually after an average period of 6 days. In about 40% of patients, this side effect is classified grade 3 (serious) or grade 4 (life-threatening) according to the National Cancer Institute Common Toxicity criteria[47]. High-dose loperamide is considered standard treatment for CPT-11-induced diarrhea in Europe and the US, but the success of this approach is limited[48].

CPT-11 is hydrolysed by hepatic carboxylesterase to its active (as an anticancer agent) metabolite, SN-38[49]. This metabolite can then be conjugated to SN-38 glucuronide (SN-38G, an inactive metabolite) by UDP-glucuronyltransferase[50]. CPT-11, SN-38, and SN-38G are excreted into the bile[50]. Once in the intestine, SN-38G can be deconjugated to SN-38 by bacterial β-glucuronidase in the cecum and colon[51]. SN-38 is believed to be responsible for CPT-11 treatment-related diarrhea[52].

In preclinical studies, when PHY906 was used in combination with CPT-11 in mice bearing Colon 38 tumors, the antitumor efficacy of the combination was greater than that of CPT-11 alone (FIG. 1A), and the toxicity (as measured by body weight loss and mortality) seen with PHY906+CPT-11 was reduced over that seen with CPT-11 alone (FIG. 1B)[53]. The reduced toxicity of the combination is also shown by Kaplan-Meyer survival curves (FIG. 2) that depict the reduced mortality of the combination vs. CPT-11 alone. Although the effects of PHY906 on CPT-induced diarrhea were not directly measured, the reduction by PHY906 of body weight loss induced by CPT-11 acts as a "surrogate" marker for diarrhea reduction. In mice bearing Colon 38 tumors and treated with a high dose of CPT-11, PHY906 proved to be much more effective in reducing body weight loss than other "antidiarrheals" including loperamide and the Chinese herbal formulations TJ-14ST, TJ-15, and PHY915[54].

The reduction in CPT-11-induced diarrhea by PHY906 may be due to its potent inhibition of bacterial β-glucuronidase (deconjugates SN-38G to SN-38, the toxic form of CPT-11) 1). Baicalein, found in *Scutellaria baicalensis* Geogi (one of the constituent herbs of PHY906) is a feedback inhibitor of β-glucuronidase (55). In addition, PHY906 contains compounds that are alternative substrates for β-glucuronidase; these could compete with SN-38G for binding to the enzyme.

On the basis of the above and other preclinical studies, an FDA-approved Phase I/IIa multicentered and randomized double-blind placebo-controlled safety study with crossover dose escalation was launched in 2002 in patients with advanced, refractory colorectal cancer. In the study, the combination of CPT-11 plus 5-fluorouracil/leucovorin (5-FU/LV) supplemented by PHY906 or placebo was used as first-line treatment. PHY906 was shown to be safe with no serious adverse events (SAEs) attributed to the study drug. PHY906 was found to have no appreciable effect on the metabolism of CPT-11 or 5-FU in controlled metabolic testing (pharmacokinetic study). Fifteen of seventeen patients treated showed either a partial response or stable disease after two courses of treatment. Reduction of diarrhea/nausea/vomiting induced by CPT-11 treatment was observed in the cross-over, internal, patient controls. PHY906 reduced the amount of loperamide necessary to treat CPT-11-induced diarrhea. At a dose of 1.2 g/day, PHY906 reduced the severity of diarrhea by one grade and, at a dose of 2.4 g/day, it reduced nausea/vomiting by one grade[56,57].

In one embodiment, the present invention provides a method of relieving side effects of a chemotherapeutic compound in a patient in need thereof comprising administering to the patient a composition comprising PHY906.

In another embodiment, the present invention provides a method of treating a bowel disorder, such as, for example, IBD and IBS, comprising administering to a patient in need thereof a therapeutically effective amount of a composition comprising an herbal preparation having Scutellaria, *Glycyrrhiza, Ziziphus* and *Paeonia*. In one preferred embodiment, the present invention provides a multiple symptoms (multisymptom) treatment for the bowel disorder. For example, the present treatment can treat or relieve at least two or more symptoms of the bowel disorder. Exemplary symptoms include, but are not limited to visceral pain, intestinal motility, inflammation, lower abdominal pain, bloating associated with alternation of bowel habits, abdominal discomfort relievable by defecation, fever, vomiting, acute diarrhea, positive stool culture, and combinations thereof.

As used herein, the term "patient" includes mammal, preferably, human. By "therapeutically effective amount", it is meant the amount of PHY906 or other active agent(s) that, when administered to a patient for treating a disease, is sufficient to effect such treatment for the disease or relief of symptoms of the disease. The "therapeutically effective amount" will vary depending on the age, weight, and severity of conditions of the patient to be treated.

In another embodiment, one or more additional active agents are co-administered to the patient for the treatment of the bowel disorder. The additional active agents can be any compound or biologics that has effect of treating the bowel disorder. Examples of the additional agent includes, but are not limited to the compound and biologics described in the Background section of this application. By "co-administering", it is meant to administer PHY906 and the additional active agent simultaneously or sequentially in such a manner to achieve a coordinated or synergistic therapeutic effect.

Opioid receptors have long been known to be involved in pain perception, but they also play other important roles. In the gut, activation of opioid receptors (by opiate drugs) in the gut wall results in decreased transit times[58]. Circular muscle contractility plays a dominant role in segmentation and peristalsis in the gut[59]. Both μ- and δ-opioid receptors are involved in neurogenic circular muscle contractions; when these receptors are activated, such contractions are inhibited[60]. In one embodiment, PHY906, at a dose of 300 μg/ml, was shown to significantly inhibit δ-opioid receptors in vitro assays.

Common symptoms of IBS and IBD include visceral pain and/or discomfort[61]. Tachykinin NK-1 receptors are believed to play an important role in mediating perception of such visceral pain (62). In addition, tachykinin NK-1 receptors are upregulated in the intestinal lamina propria of mice with IBD and thus are involved in the inflammatory cascade that that triggers and maintains intestinal lesions of IBD[63]. As indicated by Table 3, four different batches of PHY906 were shown to inhibit tachykinin NK-1 by using a radioligand binding assay with human recombinant CHO cells.

TABLE 3

Inhibition of Tachykinin NK-1 by PHY906.

| Batch No. | IC$_{50}$ (μg/ml) | K$_i$ (μg/ml) |
| --- | --- | --- |
| 906-6 | 263 | 144 |
| 906-7 | 247 | 135 |
| 906-8 | 486 | 265 |
| 906-9 | 430 | 235 |

Methods for the Tachykinin NK-1 Assay:
Human recombinant CHO cells were incubated in 20 mM HEPES buffer pH 7.4 with 1 mM MnCl$_2$ and 0.01% bovine serum albumin and reacted with the ligand 0.25 nM [$^3$H] SR-140333 according to the method of Patacchini and Maggi[70]. The non-specific ligand was 2 μM L703606. IC 50 values were determined by a non-linear, least squares regression analysis using Data Analysis Toolbox™ MDL Information Systems, San Leandro, Calif.). K. values were calculated according to the equation of Cheng and Prusoff[71].

In one embodiment, the present invention provides a method of inhibiting a 6-opioid receptor and/or a tachykinin NK-1 receptor by contacting the 6-opioid and tachykinin NK-1 receptors with a composition comprising PHY906. The 8-opioid receptor and/or a tachykinin NK-1 receptor can be present in a cell, tissue, or organism. In another embodiment, the present invention provides a method of treating a disease or condition associated with a disregulated 6-opioid receptor or tachykinin NK-1 receptor comprising administering to a patient in need thereof a therapeutically effective amount of a composition comprising PHY906.

Dysregulated cytokine production and signaling mechanisms by epithelial cells, mucosal lymphocytes, and macrophages in the gut have been implicated in the pathogenesis of both Crohn's and UC[64]. In models of Crohn's disease, the production of large amounts of cytokines such as interferon-y (IFN-y) and tumor necrosis factor (TNF), whose promoters are regulated by the transcription factor nuclear factor KB (NF-KB), is a major feature of the inflammation (65, 66) Thus, downregulation of NF-KB activity appears to be a potential key event in the control of chronic intestinal inflammation[67] Inhibition of NF-KB activity has been suggested as a major component of the anti-inflammatory activity of glucocorticoids used to treat chronic intestinal inflammation (68-69) As shown in FIG. 3, PHY906 has inhibitory activity against both intrinsic and TNF-activated NF-KB; this implies that PHY906 also has anti-inflammatory activity and may be useful as a treatment for the chronic intestinal inflammation that characterizes IBD.

In one embodiment, the present invention provides a method of inhibiting a nuclear factor-kappa B (NF-KB) by contacting the NF-icB with a composition comprising PHY906. The NF-KB can be present in a cell, tissue, or organism. In another embodiment, the present invention provides a method of treating a disease or condition associated with a disregulated NF-KB comprising administering to a patient in need thereof a therapeutically effective amount of a composition comprising PHY906.

While the present invention has been particularly shown and described with respect to preferred embodiments thereof, it will be understood by those skilled in the art that the foregoing and other changes in forms and details may be made without departing from the spirit and scope of the invention. It is therefore intended that the present invention not be limited to the exact forms and details described and illustrated but fall within the scope of the appended claims.

Furthermore, all publications cited herein are incorporated by reference in their entirety to the same extent as if each individual publication was specifically and individually indicated to be incorporated by reference.

REFERENCES

1. Loftus EV (2004). Clinical epidemiology of inflammatory bowel disease: incidence, prevalence, and environmental influences. Gastroenterology 126:1504-17.
2. Kozak I A Owings M F, Hall M J (2005). National hospital discharge survey: 2002 annual summary with detailed diagnosis and procedure data. Natl. Center for Health Statistics. Vital Heath Stat. 13(158).
3. Burt C W, Schappert S M (2004). Ambulatory care visits to physician offices, hospital outpatient departments, and emergency departments: United States, 1999-2000. Natl. Center for Health Statistics. Vital Heath Stat. 13(157).
4. Collins J G (1997). Prevalence of selected chronic conditions: United States, 1990-1992. Natl. Center for Health Statistics. Vital Heath Stat. 10(194).
5. Aminosalicylates. Crohn's and Colitis Foundation of America (CCFA) Website, updated February, 2006. Available at: http.//www.ecfa.org-info/treatment/amninosalicylates.
6. Corticosteroids. Crohn's and Colitis Foundation of America (CCFA) Website, updated February, 2006. Available at: http://www.ecfa.org/info/treatment/corticosterids.
7. Immunomodulators. Crohn's and Colitis Foundation of America (CCFA) Website, updated February, 2006. Available at: http://www.ecfa.org/info/treatment/immunomodulators.
8. Antibiotics. Crohn's and Colitis Foundation of America (CCFA) Website, updated February, 2006. Available at: http:/www.ecfa.org/info/treatment/antibiotics.
9. Biologics. Crohn's and Colitis Foundation of America (CCFA) Website, updated February, 2006. Available at: http://www.ecfa.org/info/treatment/biologics.
10. Surgery for Ulcerative Colitis. Crohn's and Colitis Foundation of America (CCFA) Website, updated February, 2006. Available at: http://www.ecfa.org/info/sugery/surgervuc.
10. Surgery for Crohn's Disease. Crohn's and Colitis Foundation of America (CCFA) Website, updated February, 2006. Available at: http://www.ecfa.org/info/surgery/surgeryed.
11. Irritable bowel syndrome. National Digestive Diseases Information Clearinghouse (NDDIC) Website, updated September, 2007. Available at: http://digestive.niddk.nih.gov/disceases/pubs/ibs/index.htm.
12. Digestive diseases statistics. National Digestive Diseases Information Clearinghouse (NDDIC) Website, updated September, 2007. Available at: http://digestive.niddlenih.gov/statistics/statistics.htm.
13. Atkinson W, Sheldon T A, Shaath N, Whorwell P J (2004). Food elimination based on IgG antibodies in irritable bowel syndrome: a randomized control trial. Gut 53:1459-1464.
14. Zar S, Mincher L, Benson M J, Kumar D (2005). Food-specific IgG4 antibody-guided exclusion diet improves symptoms and rectal compliance in irritable bowel syndrome. Scand. J. Gastroenterol. 40:800-807.
15. Van Vorous H. Irritable Bowel Syndrome Diet & IBS Recipes. Help for IBS Website, updated October, 2007. Available at: httpi/www HelpForiBS.com.
16. Caldarella M P, Milano A, Laterza F, Sacco F, et al. (2005). Visceral sensitivity and
symptoms in patients with constipation- or diarrhea-predominant irritable bowel syndrome (IBS): effect of a low-fat intraduodenal infusion. Amer. J. Gastroenterol. 100:383-389.
17. Francis C Y, Whorwell P J (1994). Bran and irritable bowel syndrome: time for reappraisal. Lancet 344:39-40.
19. Choi Y (2003). Fats, fructose may contribute to IBS symptoms. ACG 68$^{th}$ Annual Scientific Meeting Abstracts 21 and 547.
18. Zar S, Benson M J, Kumar D (2005). Food-specific IgG4 and IgE titers to common food antigens in irritable bowel syndrome. Amer. J. Gastroenterol. 100:1550-1557.

19. Quigley E M (2006). Germs, gas and the gut: the evolving role of enteric flora in IBS. *Amer. J. Gastroenterol.* 101:334-335.
20. Sharara A L, Aoun E, Abdul-Baki H, Mounzer R (2006). A randomized double-blind placebo-controlled trial of rifaximin in patients with abdominal bloating and flatulence. *Amer. J. Gastroenterol.* 101:326-333.
21. Niedzielin K, Kordecki H, Birkenfield B (2001). A controlled, double-blind, randomized study on the efficacy of *Lactobacillus plantarum* LP299V in patients with irritable bowel syndrome. *Europ. J. Gastroenterol. Hepatol.* 13:1143-1147.
22. New Studies Examine the Evidence of Probiotics on IBS. American College of Gastroenterology Website, Press Release dated Oct. 31, 2005. Available at: http://ww.acg.gi.org/media-releases/ACGO5Release Probiotic-sinIBS.pdf.
23. Probiotics for Irritable Bowel Syndrome, ClinicalTrials.gov Website. ClinicalTrials.gov Identifier NCT00355810. Available at: http://www.clinicaltrials.gov/et/action/GetStudy.
24. Efficacy of an Encapsulated Probiotic *BOdobacterium Infantis* 35624 in Irritable Bowel Syndrome. ClinicalTrials.gov Website. ClinicalTrials.gov Identifier NCT00135031. Available at: http://wwvw.clinicaltrials.gov/et/action/GetStudy.
27. Study to Determine the Effectiveness of the Probiotic *E. coli* Strain M17 in Treating Irritable Bowel Syndrome (IBS). CinicalTrials.gov Website. ClinicalTrials.gov Identifier NCT00194922. Available at: http://www.clinicaltrials.gov/et/action/GetStudy.
25. The Effect of Probiotics on Bloating in IBS. ClinicalTrials.gov Website. ClinicalTrials.gov Identifier NCT00368758. Available at: http://www.clinicaltrials.gov/et/action/GetStudy.
26. Dose Ranging Study with the Probiotic Combination (VSL #3) in Diarrhea IBS. ClinicalTrials.gov Website. ClinicalTrials.gov Identifier NCT00179582. Available at: http://www.clinicaltrials.gov/et/action/GetStudy.
27. Sung J J (2002). Acupuncture for gastrointestinal disorders: myth or magic. *Gut* 51:617619.
28. Schneider A, Enck P, Streitburger K, et al. (2006). Acupuncture treatment in irritable bowel syndrome. *Gut* 55:649-654.
29. Acupuncture for Irritable Bowel Syndrome. ClinicalTrials.gov Website. ClinicalTrials.gov Identifiers NCT00065403 and NCT00093327. Available at: http.//www.clinicaltrials.gov/et/action/GetStudy.
30. Bensoussan A, Talley N J, Hing M, et al. (1998). Treatment of irritable bowel syndrome with Chinese herbal medicine: a randomized controlled trial. *J. Amer. Med. Assoc.* 280:1585-1589.
31. Leung W K, Wu J C, Liang S M, et al. (2006). Treatment of diarrhea-predominant irritable bowel syndrome with traditional Chinese herbal medicine: a randomized placebo-controlled trial. *Am. J. Gastroenterol.* 101:1574-1580.
35. Okada F (1996). Kampo medicine: a source of drugs waiting to be exploited. *Lancet* 348:56.
32. Ernst E, Pittler M H (2002). Herbal Medicine. *Med. Clin. North Amer.* 86:149-161.
33. Cheng Y C (2001). What it takes to bring herbal medicine into mainstream medicine of the 21st century: a personal perspective. Life Resource Publ. Co., Hong Kong. pp. 27-35.
34. Wong R, Sagar C M, Sagar S M (2001). Integration of Chinese medicine into supportive cancer care: a modern role for an ancient tradition. *Cancer Treat. Rev.* 27:235-246.
35. Hsu H Y, Hsu C S (1980). Commonly Used Chinese Herb Formulas—with illustrations. Oriental Healing Art Inst., Los Angeles.
36. Chinese Botany (1999).: Shanghai Science and Technology Publ., Shanghai, $2^{nd}$ ed., Vol 7.
37. Kawato Y, Aonuma M., Hirota Y, et al. (1991). Intracellular roles of SN-38, a metabolite of the camptothecin derivative, in the antitumor effect of CPT-11. *Cancer Res.* 51:4187-4191.
38. Saltz L B. Cox J V, Blanke C, et al. (2000). Irinotecan plus fluorouracil and leucovorin for metastatic colorectal cancer. *New Engl. J. Med.* 343:905-914.
39. Colon Cancer (PDQ®): Treatment—Health Professional Version. National Cancer Institute, U.S. National Institutes of Health Website, updated April. Available at: http://www.cancer.gov/cancertopics/pdq/treatment/colon/HealthProfessional/page4.
40. Cunningham D. Pyrrhonen S, James R, et al. (1998). Randomized trial of irinotecan plus supportive care versus supportive care alone after fluorouracil failure for patients with metastatic colon cancer. *Lancet* 352:1413-1418.
45. Rougier P, Bugat R, Douillard J Y, et al. (1997). Phase 11 study of irinotecan in the treatment of advanced colorectal cancer in chemotherapy-naive patients and patients pretreated with fluorouracil-based chemotherapy. *J. Clin. Oncol.* 15:251-260.
41. Sargent D J, Niedzwiecki D, O'Connell M J, Schilsky R L (2001) Recommendation for caution with irinotecan, fluorouracil, and leucovorin for colorectal cancer. *New Engl. J. Med.* 345:144-145.
42. Hecht J R (1998). Gastrointestinal toxicity of irinotecan. *Oncology* 12:72-78.
43. Rothenberg M L, Cox J V, DeVore R F, el al. (1999). A multicenter, phase II trial of weekly irinotecan (CPT-11) in patients with previously treated colorectal carcinoma. *Cancer* 85:786-795.
44. Rivory L P, Bowles M R, Robert J, Pond S M (1996). Conversion of irinotecan (CPT-11) to its active metabolite, 7-ethyl-10-hydroxycamptothecin (SN-38) by human liver carboxylesterase. *Biochem. Pharinacol.* 52:1103-1111.
45. Atsumi R, Suzuki W, Hakusui H (1991). Identification of the metabolites of irinotecan, a new derivative of camptothecin, in rat bile and its biliary excretion. *Xenobiotica* 21:11591169.
46. Takasuna K. Hagiwara T, Hirohashi M, et al. (1996). Involvement of β-glucuronidase in intestinal microflora in the intestinal toxicity of the antitumor camptothecin derivative irinotecan hydrochloride (CPT-11) in rats. *Cancer Res.* 56:3752-3757.
47. Araki E, Ishikawa M, Iigo M, el al. (1993). Relationship between development of diarrhea and the concentration of Sn-38, an active metabolite of CPT-11, in the intestine and blood plasma of athymic mice following intraperitoneal administration of CPT-11. *Jpn. J. Cancer Res.* 84:697-702.
53. Liu S H, Jiang Z, Cheng Y C (2001). A Chinese medicine formulation, PHY906 can enhance the therapeutic index of CPT-11 and other anticancer drugs against cancer in mice. *Proc. Amer. Assoc. Cancer Res.* 42:458.

1. Liu S H, Jiang Z, Liddil J, et al. (2000). Prevention of CPT-11 induced toxicity by a Chinese medicinal formulation, PHY-906. *Proc. Amer. Assoc. Cancer Res.* 41:2608.
2. Narita M, Naga E, Hagiwara H, et al. (1993). Inhibition of beta-glucuronidase by natural glucuronides of Kampo medicines using glucoronide of SN-38 (7-ethyl-10-hydroxycamptothecin) as a substrate. *Xenobiotica* 23:5-10.
3. Farrell M P, Kummar S (2003). Phase 1/11A randomized study of PHY906, a novel herbal agent, as a modulator of chemotherapy in patients with advanced colorectal cancer. *Clin. Colorectal Cancer* 2:253-256.
4. Chu E, Yen Y, Rose M, et al. (2006). PHY906 in advanced colorectal and hepatocellular cancer clinical trials. *Proc. Fifth Mtg. of Consortium for Globalization of Chinese Medicine* p. 52.
5. Bianchi G, Ferretti P, Recchia M, et al. (1983). Morphine tissue levels and reduction of gastrointestinal transit in rats. Correlation supports primary action site in the gut. *Gastroenterology* 85:852-858.
6. Kosterlitz H W, Lees G M (1964). Pharmacological analysis of intrinsic intestinal reflexes. *Pharmacol. Rev.* 16:301-309.
7. Gray A C, White P J, Coupar I M (2005). Characterisation of opioid receptors involved in modulating circular and longitudinal muscle contraction in the rat ileum. Br. J. Pharmacol. 144:687-694.
61. Naliboff B D, Munakata J, Fullerton S, et al. (1997). Evidence for two distinct perceptual alterations in irritable bowel syndrome. *Gut* 41:505-512.
48. Okano S, Ikeura Y, Inatomi N (2002). Effects of tachykinin N K, receptor antagonists on the viscerosensory response caused colorectal distention in rabbits. *J. Pharmacol. Expl. Ther.* 300:925-931.
49. Sonea I M, Palmer M V, Akili D, Harp J A (2002). Treatment with neurokinin-1 receptor antagonist reduces severity of inflammatory bowel disease induced by *Cryptospiridium parvum. Clin. Diag. Lab. Immunol.* 9:333-340.
50. Strober W, Neurath M F (1995). Immunological diseases of the gastrointestinal tract. In: Rich R R, ed. *Clinical Immunology*. St. Louis, Mosby. Pp. 1401-1428.
51. Strober W, Kelsall B L, Fuss I, et al. (1997). Reciprocal IFN-y and TGF-I3 responses regulate the occurrence of mucosal inflammation. Immunol. Today 18:61-64.
52. van Dullemen, van Deventer S J H, Hommes D W, et al. (1995). Treatment of Crohn's disease with anti-tumor necrosis factor chimeric monclonal antibody. Gastroenterology 109:129-135.
53. Neurath M F, Becker C, Barbulescu K (1998). Role of NF-icB in immune and inflammatory responses in the gut. Gut 43:856-860.
54. Scheinman R I, Cogswell P C, Lofquist A K, et al. (1995). Role of transcriptional activation of IKBa in mediation of immunosuppression by glucocorticoids. Science 270:283-286.
55. Auphan N, DiDonato J A, Rosette C, et al. (1995). Immuno-suppression by glucocorticoids: inhibition of NF-icB activity through induction of IKBct synthesis. *Science* 270:286-290.
70. Patachini R, Maggi C A (1995). Tachykinin receptors and receptor subtypes. *Arch. Int. Phannacodyn.* 329:161-184.
56. Cheng Y, Prusoff W H (1973). Relationship between the inhibition constant ($K_1$) and the concentration of inhibitor that causes 50 percent inhibition ($I_{50}$) of an enzymatic reaction. *Biochem. Pharmacol.* 22:3099-3108.

We claim:

1. A method of treating a bowel disorder comprising administering to a patient in need thereof a therapeutically effective amount of a composition comprising an herbal preparation consisting essentially of *Scutellaria baicalensis, Glycyrrhiza uralensis, Ziziphus jujuba* and *Paeonia lactiflora*.

2. The method of claim 1, which treats multiple symptoms of the bowel disorder.

3. The method of claim 2, wherein the multiple symptoms comprises two or more symptoms selected from the group consisting of visceral pain, intestinal motility, inflammation, lower abdominal pain, bloating associated with alternation of bowel habits, abdominal discomfort relievable by defecation, fever, vomiting, acute diarrhea, positive stool culture, and combinations thereof.

4. The method of claim 1, wherein the bowel disorder is inflammatory bowel disease (IBD) or irritable bowel syndrome (IBS).

5. The method of claim 4, wherein the inflammatory bowel disease comprises a condition selected from the group consisting of Crohn's disease, ulcerative colitis (UC), collagenous colitis, lymphocytic colitis, ischaemic colitis, diversion colitis, Behcet's syndrome, infective colitis, indeterminate colitis, and combinations thereof.

6. The method of claim 4, wherein the irritable bowel syndrome comprises a condition selected from the group consisting of diarrhea-predominant IBS, constipation-predominant IBS, alternating stool pattern IBS, post-infective IBS, and combinations thereof.

7. The method of claim 1, further comprising co-administering to the patient in need thereof a therapeutically effective amount of at least one additional active agent.

8. The method of claim 7, wherein the additional active agent is selected from the group consisting of an aminosalicylate, a corticosteroid, an immunomodulator, an antibiotic, a biologic, and combinations thereof.

9. The method of claim 7, wherein the additional active agent is selected from the group consisting of a stool softener, a laxative, an antidiarrheal, an opioid or opioid analog, a tricyclic, a selective serotonin reuptake inhibitor, a probiotic, and combinations thereof.

10. The method of claim 1, further comprising acupuncture or surgery.

11. The method according to claim 1 wherein said herbal preparation is a mixture of *Scutellaria baicalensis, Glycyrrhiza uralensis, Ziziphus jujuba* and *Paeonia lactiflora* in a weight ratio of 1.5:1:1:1.

12. The method according to claim 2 wherein said herbal preparation is a mixture of *Scutellaria baicalensis, Glycyrrhiza uralensis, Ziziphus jujuba* and *Paeonia lactiflora* are mixed together in said herbal preparation in a weight ratio of 1.5:1:1:1.

13. The method according to claim 3 wherein said herbal preparation is a mixture of *Scutellaria baicalensis, Glycyrrhiza uralensis, Ziziphus jujuba* and *Paeonia lactiflora* in a weight ratio of 1.5:1:1:1.

14. The method according to claim 4 wherein said herbal preparation is a mixture of *Scutellaria baicalensis, Glycyrrhiza uralensis, Ziziphus jujuba* and *Paeonia lactiflora* in a weight ratio of 1.5:1:1:1.

15. The method according to claim 5 wherein said herbal preparation is a mixture of *Scutellaria baicalensis, Glycyrrhiza uralensis, Ziziphus jujuba* and *Paeonia lactiflora* in a weight ratio of 1.5:1:1:1.

16. The method according to claim 6 wherein said herbal preparation is a mixture of *Scutellaria baicalensis, Glycyrrhiza uralensis, Ziziphus jujuba* and *Paeonia lactiflora* in a weight ratio of 1.5:1:1:1.

17. The method according to claim 7 wherein said herbal preparation is a mixture of *Scutellaria baicalensis, Glycyrrhiza uralensis, Ziziphus jujuba* and *Paeonia lactiflora* in a weight ratio of 1.5:1:1:1.

18. The method according to claim 1 wherein said herbal preparation is a mixture of *Scutellaria baicalensis, Glycyrrhiza uralensis, Ziziphus jujuba* and *Paeonia lactiflora* in a weight ratio of about 0.286:about 0.214:about 0.286:about 0.214.

19. The method according to claim 2 wherein said herbal preparation is a mixture of *Scutellaria baicalensis, Glycyrrhiza uralensis, Ziziphus jujuba* and *Paeonia lactiflora* are mixed together in said herbal preparation in a weight ratio of about 0.286:about 0.214:about 0.286:about 0.214.

20. The method according to claim 3 wherein said herbal preparation is a mixture of *Scutellaria baicalensis, Glycyrrhiza uralensis, Ziziphus jujuba* and *Paeonia lactiflora* in a weight ratio of about 0.286:about 0.214:about 0.286:about 0.214.

21. The method according to claim 4 wherein said herbal preparation is a mixture of *Scutellaria baicalensis, Glycyrrhiza uralensis, Ziziphus jujuba* and *Paeonia lactiflora* in a weight ratio of about 0.286:about 0.214:about 0.286:about 0.214.

22. The method according to claim 5 wherein said herbal preparation is a mixture of *Scutellaria baicalensis, Glycyrrhiza uralensis, Ziziphus jujuba* and *Paeonia lactiflora* in a weight ratio of about 0.286:about 0.214:about 0.286:about 0.214.

23. The method according to claim 6 wherein said herbal preparation is a mixture of *Scutellaria baicalensis, Glycyrrhiza uralensis, Ziziphus jujuba* and *Paeonia lactiflora* in a weight ratio of about 0.286:about 0.214:about 0.286:about 0.214.

24. The method according to claim 7 wherein said herbal preparation is a mixture of *Scutellaria baicalensis, Glycyrrhiza uralensis, Ziziphus jujuba* and *Paeonia lactiflora* in a weight ratio of about 0.286:about 0.214:about 0.286:about 0.214.

* * * * *